United States Patent [19]
Hashimoto et al.

[11] Patent Number: 5,474,989
[45] Date of Patent: Dec. 12, 1995

[54] DRUG COMPOSITION

[75] Inventors: Masanori Hashimoto, Yamato; Masaki Otagiri; Teruko Imai, both of Kumamoto, all of Japan

[73] Assignee: Kurita Water Industries, Ltd., Tokyo, Japan

[21] Appl. No.: 203,863

[22] Filed: Mar. 1, 1994

Related U.S. Application Data

[63] Continuation of Ser. No. 945,446, Sep. 14, 1992, abandoned, which is a continuation of Ser. No. 684,950, May 3, 1991, abandoned.

[30] Foreign Application Priority Data

Nov. 11, 1988 [JP] Japan ................... 63-285566

[51] Int. Cl.$^6$ .................. A61K 31/73; A61K 31/56; A61K 31/40; A61K 31/355
[52] U.S. Cl. ............... 514/55; 514/179; 514/420; 514/458; 514/560; 514/570; 514/650
[58] Field of Search ............... 514/55, 179, 420, 514/560, 570, 650, 458

[56] References Cited

U.S. PATENT DOCUMENTS 4,946,870  8/1990  Partain, III et al. ............... 514/55

OTHER PUBLICATIONS

Chemical Abstracts (103: 92752t) 1985.
Chemical Abstracts (106: 182672h) 1987.
Chemical Abstracts (109: 197081a) 1988.

*Primary Examiner*—Raymond Henley, III
*Assistant Examiner*—Kevin E. Weddington
*Attorney, Agent, or Firm*—Flynn, Thiel, Boutell & Tanis

[57] ABSTRACT

The present invention relates to a drug composition in which the solubility and the dissolution rate of a drug having low water solubility are improved by incoroprating therein a low molecular weight chitosan in an amount of from 0.2 to 10 parts by weight per one part by weight of the poorly water-soluble drug. As the low molecular weight chitosan, those having a weight average molecular weight in the range from 500 to 50,000 and soluble in water were employed. This drug composition is prepared by mixing the components intimately so as to obtain a homogeneous dispersion of the low molecular weight chitosan with the mass of the composition.

The drug composition according to the invention can be worked up into various preparation forms, such as, granules etc., as medicaments for administration to living organisms in which the bioabsorptivity and biouptake are improved.

10 Claims, 11 Drawing Sheets

Fig. 5(A) Triamcinolone

Fig. 5(B) Betamethasone

Fig. 5(C) Prednisolone

Fig. 5(D) Flurbiprofen

Fig. 5(E) Indomethacin

Fig. 5(F) Digoxin

Fig. 5(G) Phenytoin

Fig. 6(A)

Flurbiprofen

Fig. 6(B)

Indomethacin

Fig. 6(C)

Digoxin

Fig. 6(D)

Triamcinolone

Fig. 8

DRUG COMPOSITION

This application is a continuation of U.S. Ser. No. 07/945,446, filed Sep. 14, 1992 now abandoned, which is a continuation of Ser. No. 07/684,950, filed May 3, 1991 now abandoned.

TECHNICAL FIELD

The present invention relates to a drug composition containing a low molecular weight chitosan and at least one poorly water-soluble drug.

TECHNICAL BACKGROUND

Medicines called poorly water-soluble drugs have very low solubility in water and, thus, exhibit a quite low "bioabsorptivity", namely, rate of absorption of drug in living organisms upon oral administration, and are often accompanied by having a poor "biouptake", that is, a low amount of drug absorbed into the body of living organisms. Therefore, attempts have been proposed for making such poorly water-soluble drugs more soluble in water by converting them into water-soluble salts e.g. sodium salt or hydrochloride salt, prescribing the drug as a water-soluble prodrug and so on. Proposals have been made also from the pharmaceutical point of view, for example, addition of a solubilizing agent, such as a surface active agent, to the drug and the enclusion of the drug particles with cyclodextrin. In a fine crystallographic technology, a micropulverization of the original drug powder and treatment for making the drug powder amorphous were also proposed.

Since however, each of these prior art measures has a preferential group of drugs in which they apply to, no practical measure generally applicable for every drug preparation has yet been proposed. It is the position of the art today, that, in particular, a proposal capable of complying with the demand of improving the biouptake of drug may not result in improving the bioadsorptivity of drug. Among the poorly water-soluble drugs however, there are many which are required to have an immediate medicinal effect, therefore, a demand still remains for pharmaceuticals for oral administration which not only have a biouptake but also a prompt bioabsorptivity.

In these circumstances, it has been proposed to utilize various high molecular weight substances for improving the bioabsorptivity of poorly water-soluble drugs.

With respect to the use of high molecular weight gelatine, Japanese Patent Application Kokai No. 26615/1982 discloses a technique of co-crushing poorly water-soluble drugs with high molecular weight gelatine etc. This technique employs a large amount of gelatine to be added for improving the bioabsorptivity of poorly water-soluble drug and has a shortcoming in that the technique is limited only to the employment of co-crushing.

On the other hand, attempts have been made for the use of chitin or chitosan obtained from the shells of crab and lobster in pharmaceutical applications. Most of the uses of chitin and chitosan have, however, been directed only to a gradual liberation of a pharmaceutical in living organisms and there is still only a few reports of the solubilization of poorly water-soluble drugs.

Japanese Patent Publication No. 28414/1988 discloses a method for improving the bioabsorptivity and the biouptake of a poorly water-soluble drugs selected from the group consisting of antibiotics and antiepileptics, by subjecting the drug to mixing and co-crushing together with chitin and/or chitosan to such an extent that most of the drug is rendered amorphous. This Japanese Patent Publication does not disclose, however, the use of low molecular weight chitosan and the method exhibits problems not only by requiring large amounts of energy consumption and extensive time for the mixing and co-crushing but by also in making the pharmaceutical process complex.

There is, on the other hand, a report as to a technical measure for improving the dissolution rate of kitasamycin by mixing it with various high molecular weight substances by a roller mixer ["Hyomen" 26 (5), 336 (1988)], in which chitosan is employed in a form of a solution of acetic acid salt, the effect of which is lower than that of polyvinylpyrrolidone as seen by a comparison of the data.

An object of the present invention is to solve the problems explained above and to provide a drug composition in which the solubility and the rate of dissolution of various poorly water-soluble drugs are improved.

Another object of the present invention is to provide a drug composition containing one or more poorly water-soluble drugs capable of being prepared in various forms by means of various pharmacological processes of wet and dry systems, co-crushing, spray granulation and so on.

DISCLOSURE OF THE INVENTION

The inventors have studied and evaluated the effect of the addition of various high molecular weight substances to drug compositions for the purpose of improving the dissolution performance of poorly water-soluble medicinal drugs and found that the solubility and the dissolution rate of poorly water-soluble drugs were improved by mixing the poorly water-soluble drugs with a low molecular weight chitosan, thereby arrived at the present invention.

Thus, the present invention relates to a drug composition containing one or more poorly water-soluble drugs and a low molecular weight chitosan.

The low molecular weight chitosan to be used in the drug composition according to the present invention is a molecular weight degraded product of chitosan derived from natural chitin, which is obtained by subjecting chitosan to a molecular weight-degrading treatment and which has a weight average molecular weight in the range of from 500 to $50 \times 10^3$, preferably in the range from 800 to $10 \times 10^3$, and is soluble not only in acidic water but also in neutral or alkaline water. If the weight average molecular weight is lower than 500 or greater than $50 \times 10^3$, the effect of improving the solubility and in the dissolution rate of the poorly water-soluble drug becomes poor. The weight average molecular weight can be determined by gel permeation chromatography using a series of polyethylene glycols of known molecular weights as the calibration standards.

The starting chitosan to be employed as the raw stock for producing the low molecular weight chitosan according to the present invention is a high molecular weight substance from the chitin obtained from shells or exoskeletons of crabs and lobsters by a deacetylation treatment thereof with alkali. The degree of deacetylation is not critical and is not specifically limited so long as the resulting raw chitosan can be dissolved in acidic water. The degree of deacetylation may, in general, be 50–100%. The low molecular weight chitosan can be obtained from such raw chitosan by various chemical methods including enzyme treatment of the raw chitosan, treatment of the raw chitosan with, such as, hydrogen peroxide, nitrite ion, an alkali or an acid, to break down the glucoside linkages.

Practical procedures for chemically obtaining the low molecular weight chitosan comprises suspending the raw chitosan in an alkaline solution, adding to the resulting suspension an adequate amount of hydrogen peroxide, effecting the reaction at a definite temperature for a definite period of time to lower the chitosan's molecular weight and subjecting the resulting reaction product to a refining process consisting of desalting, molecular weight fractionation and so on, followed by dewatering, drying and pulverization of the purified product. The reaction of the raw chitosan with hydrogen peroxide may preferably be carried out at a pH of b–12, a concentration of hydrogen peroxide of 0.005–10% by weight, a reaction temperature of 20°–90° C. and a reaction duration of about 30–500 minutes.

With respect to enzyme treatment, the raw chitosan is contacted with a chitinase or with a chitosanase to cause degradation of the chitosan's molecular weight, whereupon the after-treatment as explained above may be employed.

As the poorly water-soluble drug to be contained in the drug composition according to the present invention, any medicament may be employed without special limitation so long as it exhibits poor or insufficient bioavailability, i.e. bioabsorptivity and biouptake. Examples of such medicaments include:

1) Hypnotics and sedatives, such as, nitrazepam, triazolam, phenobarbital, amobarbital, etc.
2) Antiepileptics, such as, phenytoin, metharbital, primidone, clonazepam, carbamazepine, valproates, etc.
3) Analgesic-antipyretic antiphlogistics, such as, flurbiprofen, mefenamic acid, ketoprofen, ibuprofen, indomethacin, diclofenac acid, phenacetin, oxyphenbutazone, phenylbutazone, sulpyrine, pentazocine, piroxicam, etc.
4) Antiemetics, such as, meclizine hydrochloride, dimenhydrinate, etc.
5) Psycholeptics, such as, haloperidol, meprobamate, chlordiazepoxide, diazepam, oxazepam, sulpiride, etc.
6) Antispasmodics, such as, papaverine, atropine, etomidoline, etc.
7) Cardiotonics, such as, digoxin, digitoxin, methyldigoxin, ubidecarenone, etc.
8) Antiarrhythmic drugs, such as, pindolol, ajmaline, disopyramide, etc.
9) Diuretics, such as, hydrochlorothiazide, spironolactone, triamterene, furosemide, bumetanide, etc.
10) Antihypertensive drugs, such as, reserpine, dihydroergotoxine mesylate, prazosin hydrochloride, metoprolol, propranolol, atenolol, etc.
11) Coronary vasodilators, such as, nitroglycerin, isosorbide dinitrate, diltiazem, nifedipine, dipyridamole, etc.
12) Antitussives, such as, noscapine, salbutamol, procaterol, tulobuterol, tranilast, ketotifen, etc.
13) Cerebral circulation improving drugs, such as, nicardipine, vinpocetine, etc.
14) Antibiotics, such as, erythromycin, josamycins, chloramphenicol, tetracycline, rifampicin, griseofulvin, etc.
15) Antihistaminics, such as, diphenhydramine, promethazine, mequitazine, etc.
16) Steroids, such as, triamcinolone, dexamethasone, betamethasone, prednisolone, danazol, methyltestosterone, chlormadinone acetate, etc.
17) Vitamins, such as, vitamin E, vitamin K, α-calcidol, phytonadione, dl-α-tocopherol nicotinate, menatetrenone, etc.
18) Others including dicumarol, cinnarizine, clofibrate, gefarnate, cimetidine, probenecid, mercaptopurine, methotrexate, ursodeoxycholic acid, dihydroergotamine mesylate, etc.

In view of the dissolution performance of the intrinsic powdery drug, the original raw stock obtained after crushing with a wet or dry crusher may preferably have an average particle size below 100 μm, preferably below 50 μm.

The drug composition according to the present invention is obtained by mixing the low molecular weight chitosan with one or more poorly water-soluble drugs. It is desirable upon mixing to attain a uniform dispersion of the low molecular weight chitosan over the entire pulverous mass of the poorly water-soluble drug. There is no special restriction as to the practical manner of such mixing. Thus, there may be used for example, simple mixing of the two essential powdery components (hereinafter, the mixture resulting from such simple mixing is expressed as a "physical mixture"), mixing under kneading of the two essential powdery components with the addition of an adequate amount of a solvent, such as water, to the mixture (hereinafter, the mixture resulting from such a kneading process is denoted as a "solid dispersion") and admixing of powder of the poorly water-soluble drug into an aqueous solution of the low molecular weight chitosan. An adequate amount of the low molecular weight chitosan may be employed during the mixing, in accordance with each specific drug to be mixed. In general, from 0.2 to 10 parts by weight of the low molecular weight chitosan are employed per one part of the poorly water-soluble drug for attaining an improvement in the solubility and dissolution rate of the drug.

The drug composition according to the present invention can be administered to humans after it has been prepared into a medicinal drug in various ways. Thus, the drug composition according to the present invention can be applied as such in the form of a granule or in a form of, such as, a tablet, capsule, paste, patch coating, suppository, syrup, troche or so on. These preparations may contain, if necessary, various additives known in the pharmaceutical arts, such as, excipients, crumbling adjuvants, lubricating agents and so on.

The drug composition according to the present invention can be worked up into various pharmaceutical preparations by the following procedures:

Tablets can be obtained, for example, in a wet process by a kneading technique, in which the low molecular weight chitosan and the poorly water-soluble drug are kneaded using a suitable solvent, such as, water, an acid solution or so on, followed by drying, grain size sorting and tabletting, or by a semidirect tabletting technique, in which the low molecular weight chitosan and the poorly water-soluble drug are kneaded, followed by drying, grain size sorting, addition of various additives and tabletting; by a dry process or by a co-crushing technique, in which the amount of the low molecular weight chitosan can be adjusted. Among them, the wet process for preparing the solid dispersion is the most preferred. While it is also preferable for the granule product and capsule product to effect the pharmacological preparation by a wet process, as in the case of tablets, a dry process and the co-crushing technique, and even a spray granulation technique, may occasionally be employed. In the case of tablets and granules, coatings can be incorporated for the purpose of masking the drug particles.

The drug products prepared as above exhibit an improved solubility and an improved rate of dissolution as compared with those of the prior art, so they are also superior in bioavailability.

According to the present invention, drug compositions exhibiting improved solubility and improved rates of dissolution of the poorly water-soluble drug, as compared with conventional drug compositions can be obtained by the incorporation of a low molecular weight chitosan in into the drug composition. These drug compositions can be worked up into various application forms by various drug preparation techniques for wet and dry processes, as a well as co-crushing technique, spray granulation technique and so on. The medicinal preparations made from the drug compositions according to the present invention offer an improvement in their bioabsorptivity and biouptake by living organisms.

BEST MODES FOR CARRYING OUT THE INVENTION

Below, the present invention will be described by way of Examples, in which % values are on the weight basis.

REFERENCE EXAMPLE 1

A crude pulverous chitosan (referred to hereinafter as C-0) was obtained from a crab *Reptantia chionoecetes* by a usual technique. From this crude pulverous chitosan, an aqueous suspension having a pH of 11.0 was prepared. To this suspension was added a varying amount of an aqueous hydrogen peroxide solution in an amount corresponding to the range of 2.1–40.0 g/l and the reaction was carried out while agitating the suspension at a temperature of 70° C. for 110–300 minutes to effect a molecular weight degradation. The reaction product was then separated and subjected to desalting, purifying and freeze drying, whereby four low molecular weight chitosan products C-1, C-2, C-3 and C-4 as shown in Table 1 were obtained. On the other hand, an amount of the crude chitosan C-0 was subjected to a similar reaction with hydrogen peroxide at a pH of 8.0, a temperature of 70° C. an initial concentration of hydrogen peroxide of 40 g/l and under agitation to effect a molecular weight degradation. After the reaction, the reaction mixture was filtered to remove solids and the filtrate was subjected to a molecular weight fractionation using a UF membrane. The resulting product was freeze dried to obtain a low molecular weight chitosan product C-5. The material properties of each of the resulting chitosan products are recited in Table 1.

The value for the evaporated residue in Table 1 is the amount of dry residue left after evaporation of an aqueous solution of the chitosan product at 105° C. The value for the ash in Table 1 corresponds to the amount of ignition residue of the chitosan product left after the burning thereof at 600° C. The molecular weight of the chitosan product was determined by gel permeation chromatography. Here, an amount of chitosan product is dissolved in an adequate amount of water containing acetic acid in an amount corresponding to that of the chitosan product, from which 2.0 ml were pipetted and diluted using a 0.2M acetic acid-0.1M sodium acetate buffer solution up to 50 ml and this was introduced into a column packed with TSK Gel 3000 PWXL (trade mark) of Toso K.K. and the column eluted with a 0.2M acetic acid-0.1M sodium acetate buffer solution. Besides, a calibration curve for the packed column was prepared beforehand using a series of polyethylene glycol products of known molecular weights. The weight average molecular weight of each of the chitosan products was determined based upon this calibration curve.

TABLE 1

| Property | Chitosan Product | | | | | |
|---|---|---|---|---|---|---|
| | C-0 | C-1 | C-2 | C-3 | C-4 | C-5 |
| Evapor. residue[1] | 92.1 | 93.7 | 93.9 | 94.2 | 98.0 | 94.0 |
| Ash[2] | 0.7 | 0.1 | 0.2 | 0.1 | 0.2 | 2.3 |
| Molecular weights[3] | 230 | 48 | 33 | 25 | 10 | 3.8 |
| Charge density[4] | 5.1 | 5.5 | 5.5 | 5.5 | 5.4 | 2.8 |

Notes:
[1] Wt. %, based on the sample weight
[2] Wt. %, based on the sample weight
[3] ×10$^3$
[4] Ionic charge in meq per gram chitosan

EXAMPLE 1

Figure 1:
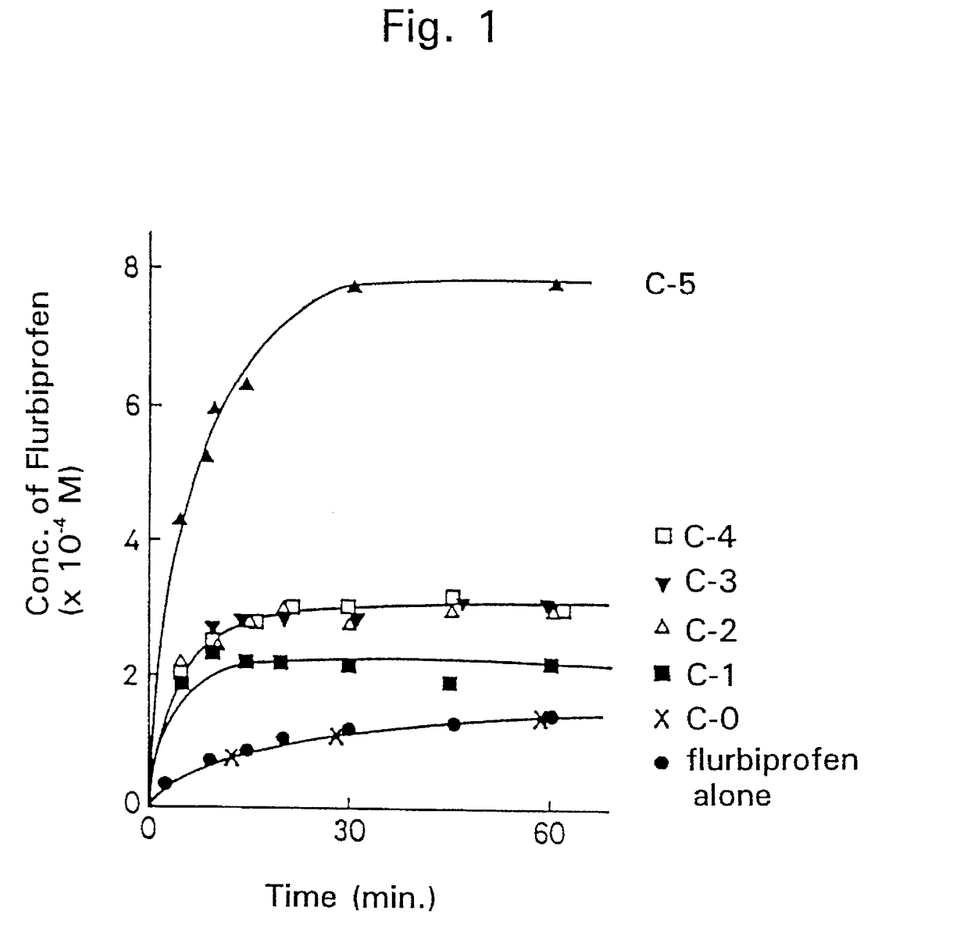
FIG. 1 is a graph representing the experimental results of Example 1.

Each 3 parts by weight of the chitosan products C-0 to C-5 was added to 1 part by weight of flurbiprofen (denoted sometimes hereinafter as FP) and the mixture kneaded with the addition of water in an amount of 2-fold of that of the chitosan product for 1 hour. The kneaded mixture was dried under a reduced pressure at room temperature for 48 hours. A fraction of the particles that passed through 100-mesh standard sieve was employed as the solid dispersion. For each of these solid dispersions, the dissolution rate of FP into water at 37° C. was observed by the procedure given below:

500 ml of water were charged in a dissolution rate measuring device (made by Toyama Sangyo Co., Ltd.) maintained at 37° C. and thereto was further added each of the above solid dispersions in an amount corresponding to 40 mg as FP and the mixture was agitated at 91 rpm. The agitated mixture was sampled each in an amount of 3 ml at a regular time interval with a pipette fitted with a cotton plug. Each sample was filtered through a 0.45 µm membrane filter and the FP concentration of the filtrate was determined after extraction with chloroform. Results are given in FIG. 1 as a graph.

EXAMPLE 2

A composition composed of vitamin E or vitamin K with the low molecular weight chitosan C-5 was prepared in the manner given below and the solubility of vitamin E or of vitamin K was determined in the manner given below.

Each 5 mg of vitamin E and vitamin K was accurately weighed (this amount is chosen so as to exceed above the solubility limits of these drugs) and placed in a test tube. To each of the test tubes, an equal amount of an aqueous solution of the chitosan product C-5, as obtained in Reference Example 1, of varying concentration was added and the test tube was tightly sealed and was shaken at 25° C. for 10 days. Each of the solutions which reached dissolution equilibrium was sampled with a pippette fitted with a cotton plug. The sample was filtered through a 0.45 μm membrane filter and the concentration of vitamin E or vitamin K was determined by means of UV-determination after extraction with chloroform.

Figure 2:
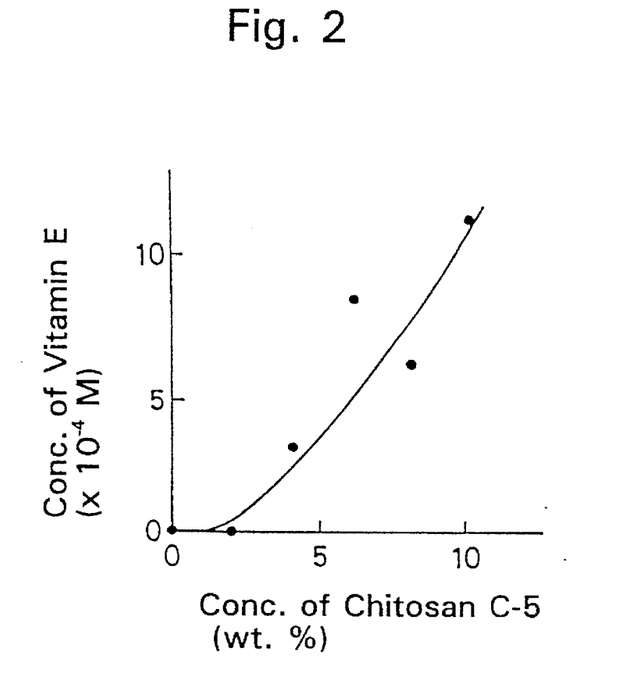
FIGS. 2 and 3 are graphs representing the experimental results of Example 2.
Figure 3:
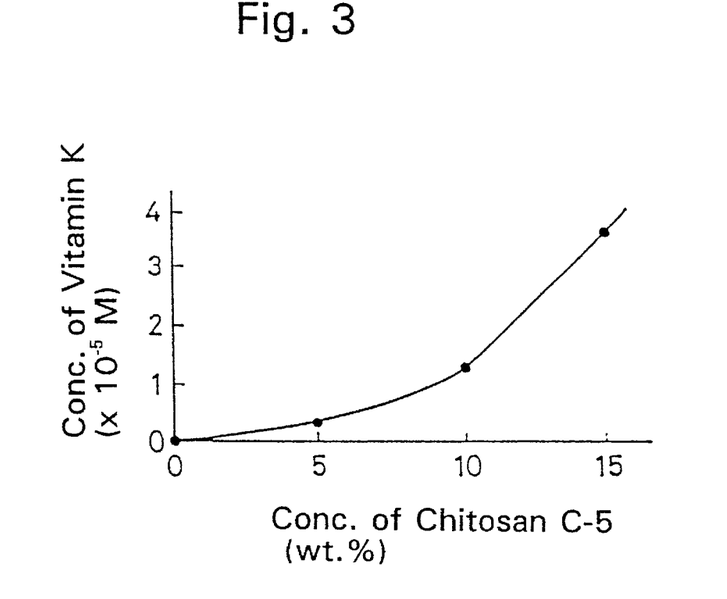
Figure 4A:
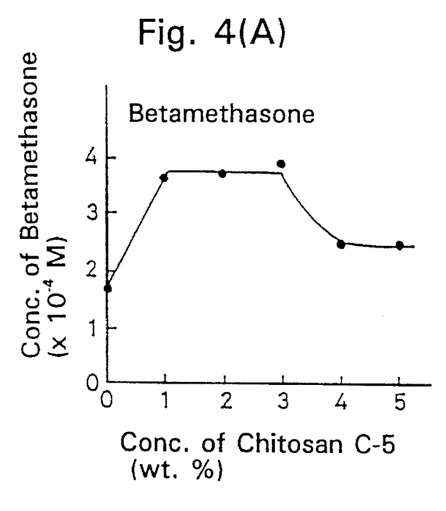
FIGS. 4(A)–(L) are graphical recitation of the experimental results of Example 3.
Figure 4B:
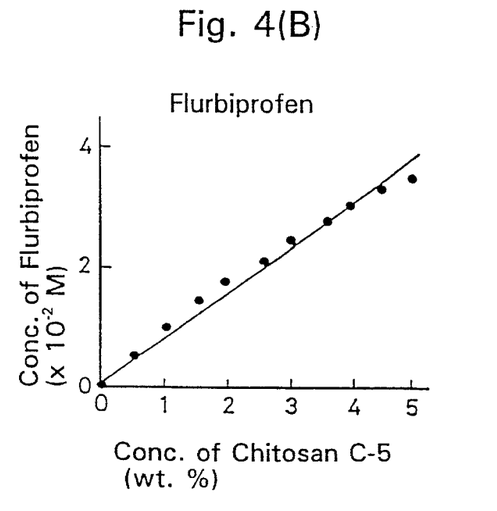
Figure 4C:
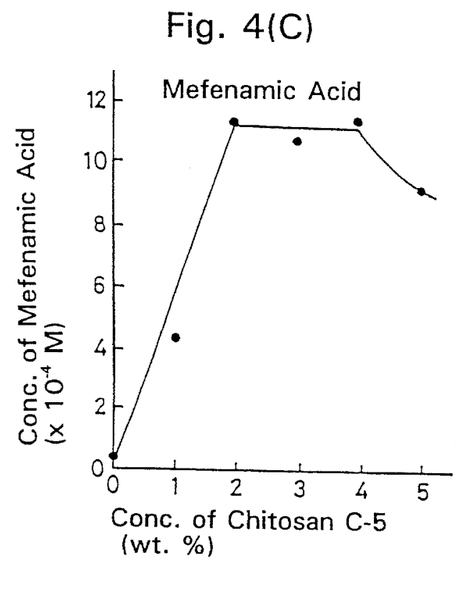
Figure 4D:
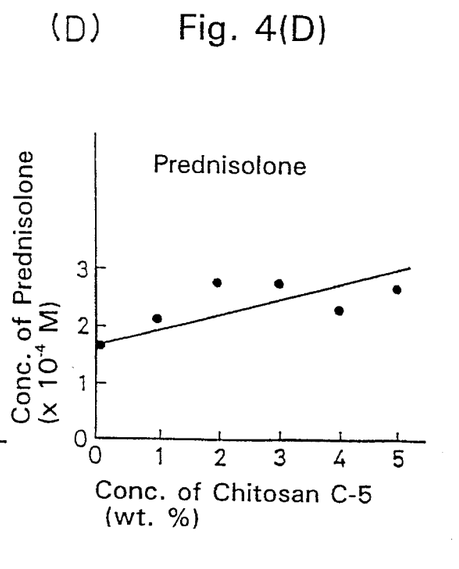
Figure 4E:
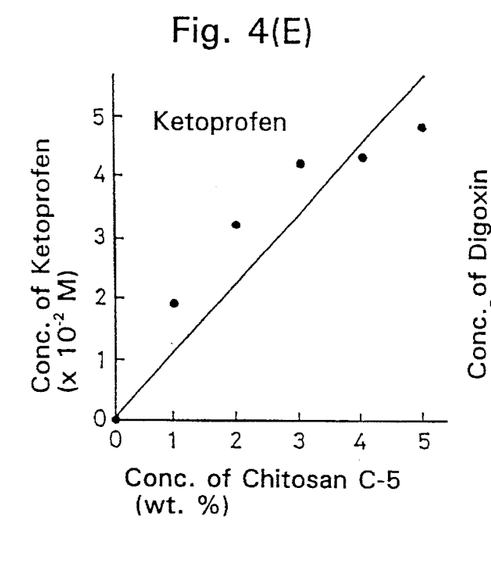
Figure 4F:
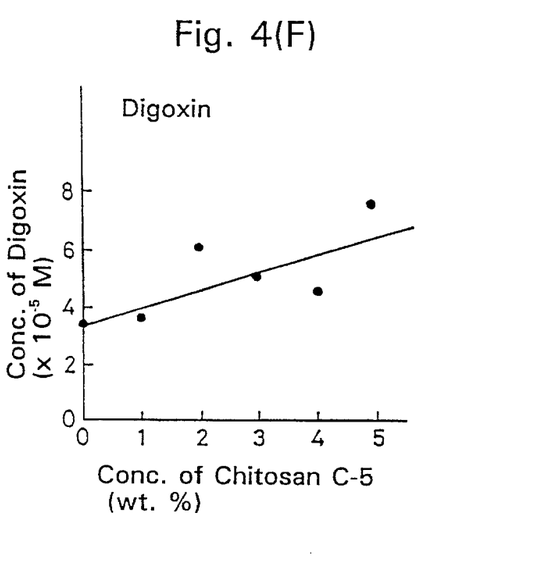
Figure 4G:
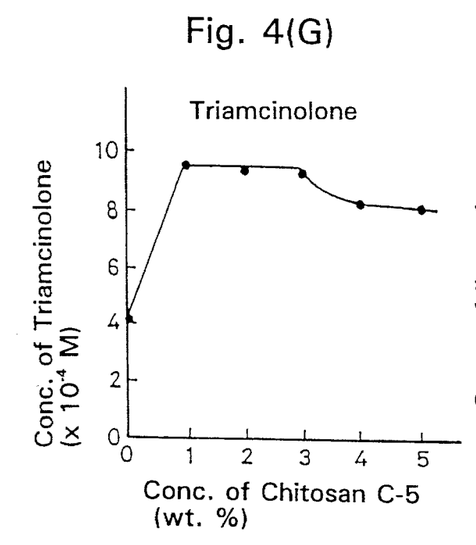
Figure 4H:
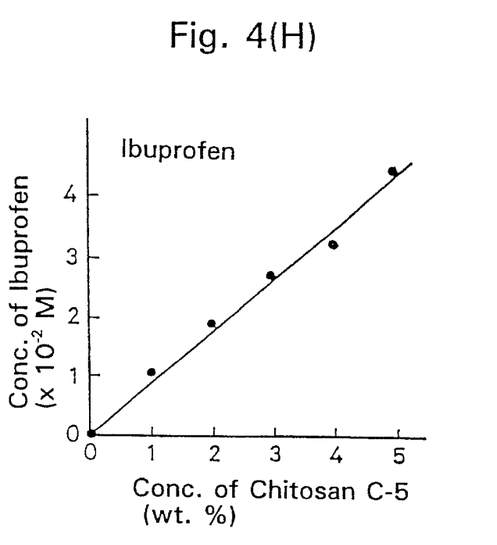
Figure 4I:
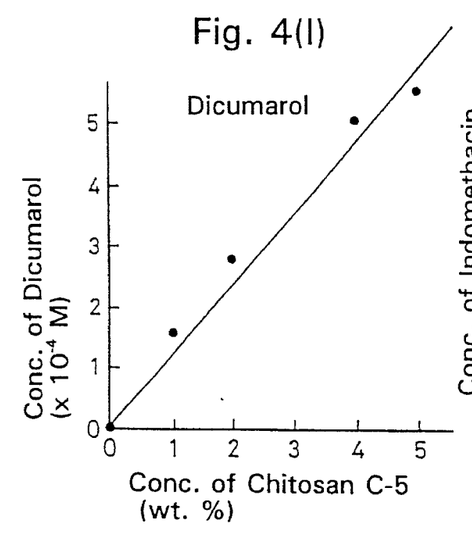
Figure 4J:
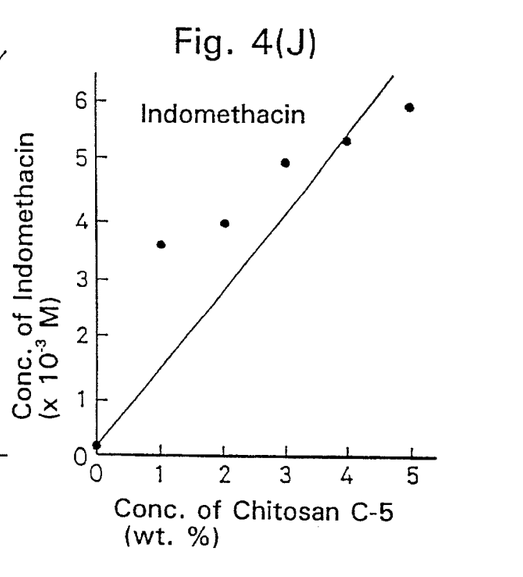
Figure 4K:
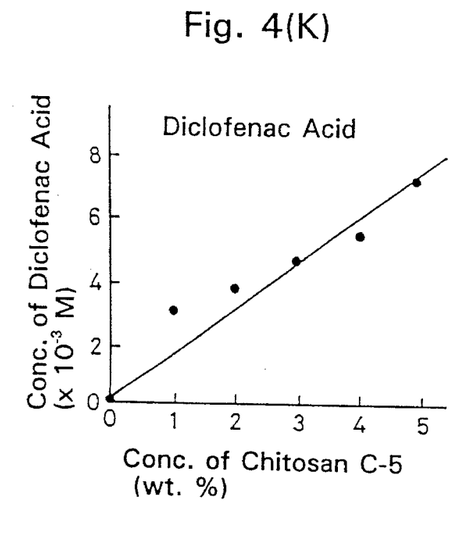
Figure 4L:
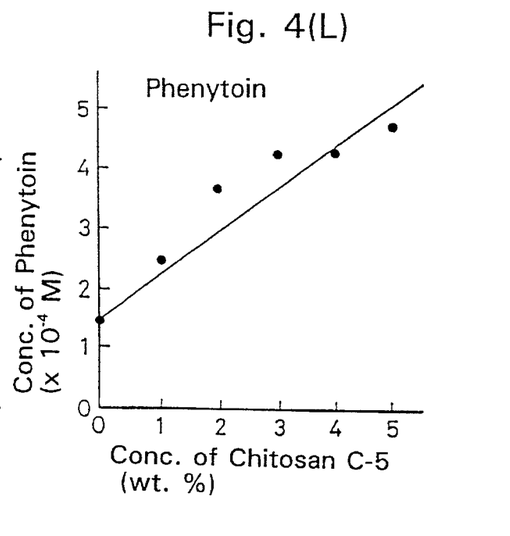
Figure 5A:
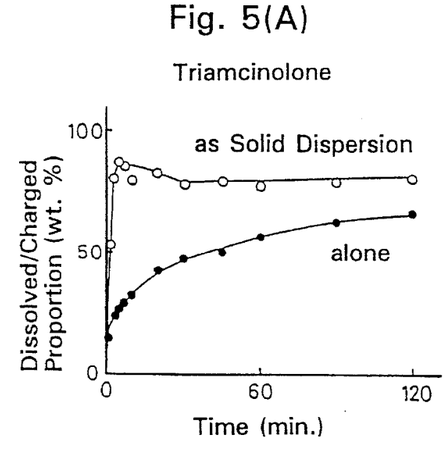
FIGS. 5(A)–(G) are graphical recitation of the experimental results of Example 4.
Figure 5B:
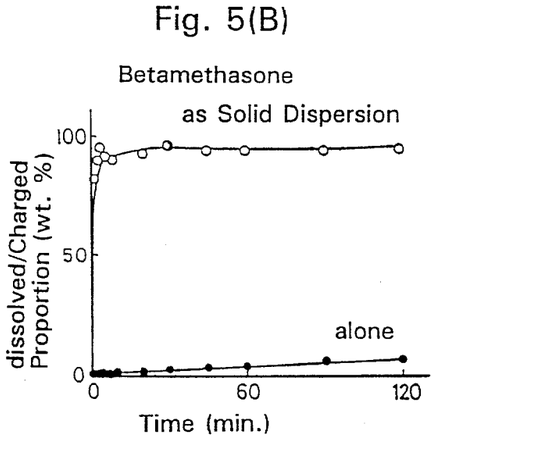
Figure 5C:
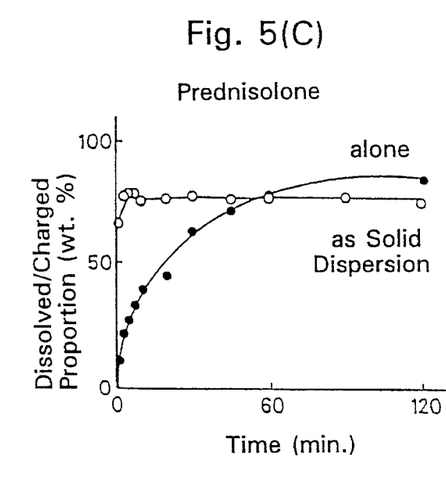
Figure 5D:
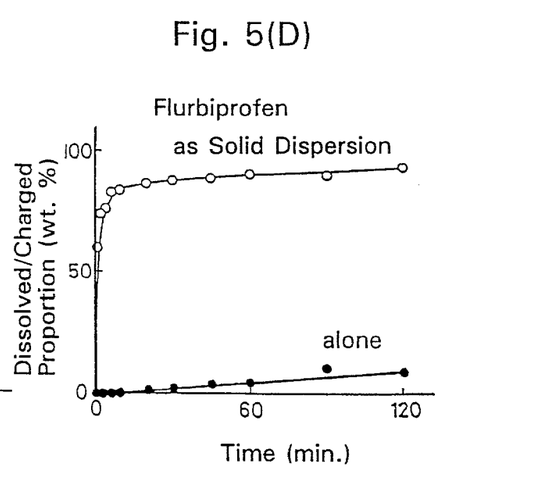
Figure 5E:
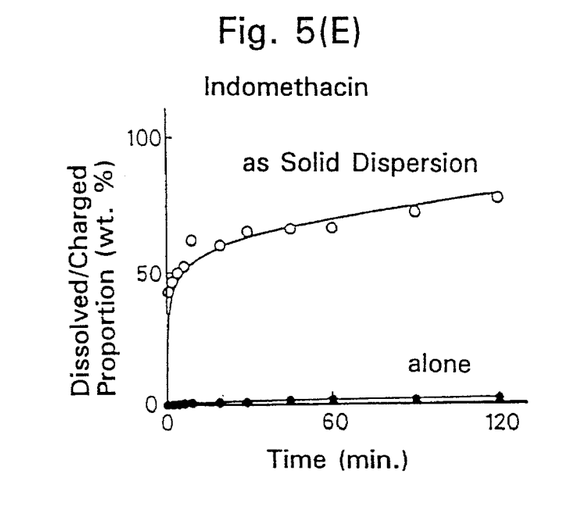
Figure 5F:
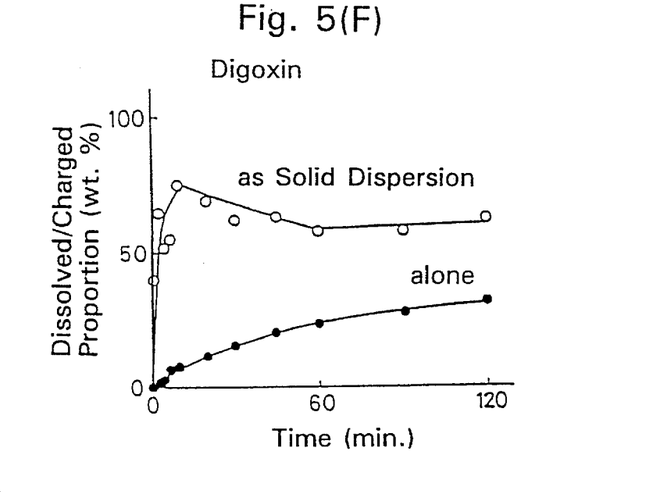
Figure 5G:
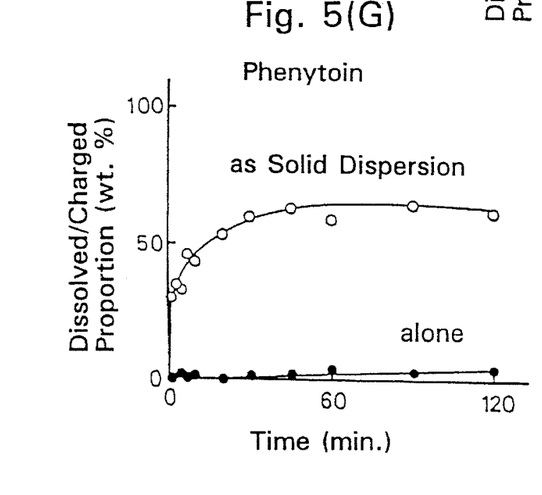
Figure 6A:
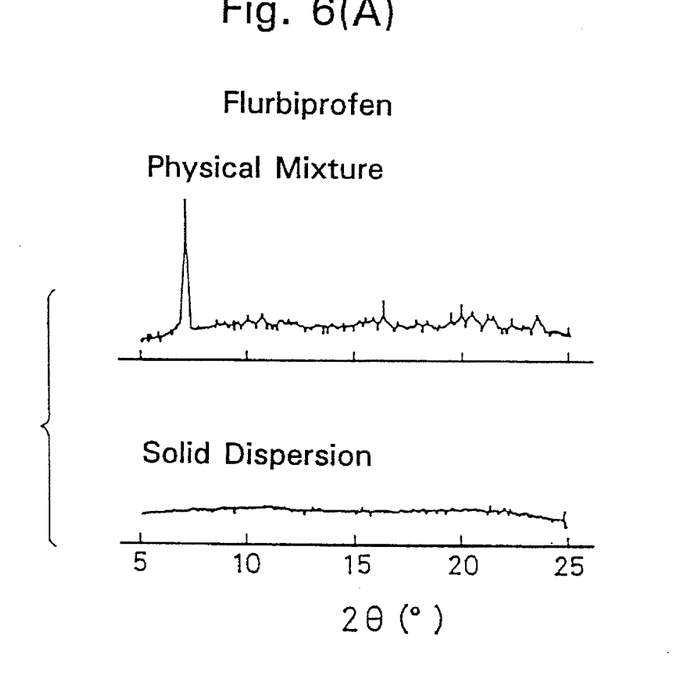
FIGS. 6(A)–(D) are graphical recitation of the experimental results of Example 5.
Figure 6B:
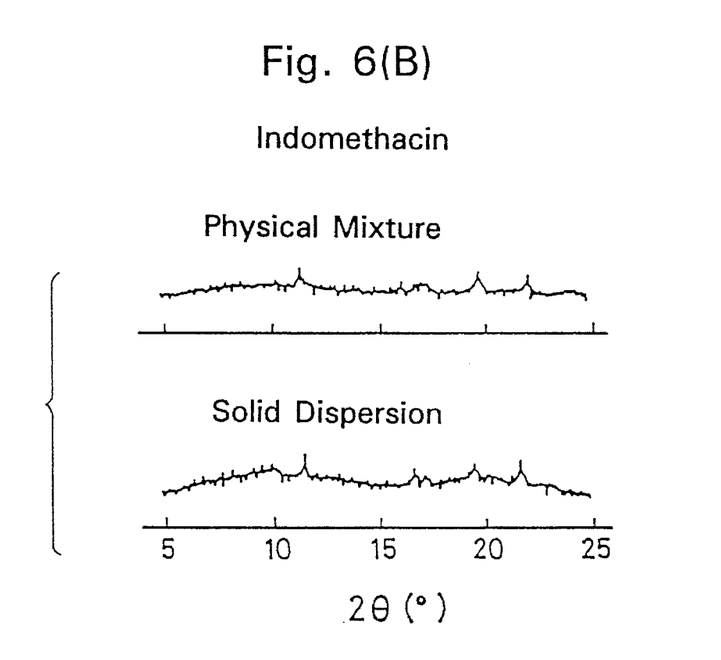
Figure 6C:
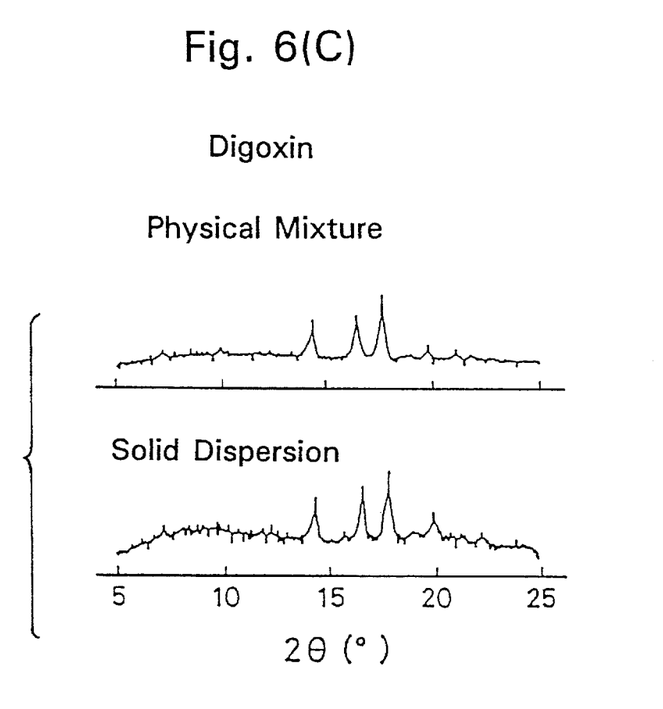
Figure 6D:
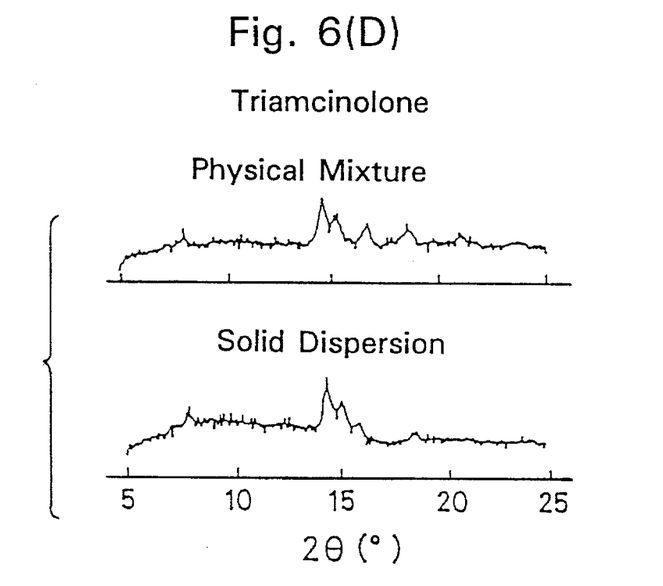

The experimental results for vitamin E are given in FIG. 2 and that for vitamin K in FIG. 3 as a graph.

EXAMPLE 3

Each of the drug compositions of poorly water-soluble drugs given in Table 2 containing the low molecular weight chitosan product C-5 was examined for the solubility of the drug in the same manner as in Example 2. The results are summarily given in FIGS. (A) to 4(L) in a respective graph.

TABLE 2

| Drug | Main Application |
| --- | --- |
| Betamethasone | Antiinflammatory |
| Flurbiprofen | Analgesic antiinflammatory |
| Mefenamic acid | Antiinflammatory analgesic |
| Prednisolone | Glucocorticoid, Antirheumatic and Antiinflammatory |
| Ketoprofen | Analgesic antiinflammatry |
| Digoxin | for Pulmonary edema and Congestive cardiac insufficiency |
| Triamcinolone | Adrenocorticotropic hormones, Antirheumatic, Antiallergic |
| Ibuprofen | Antifebrile antiinflammatory analgesic |
| Dicumarol | Antiblood-coagulant |
| Indomethacin | Antiinflammatory analgesic antifebrile |
| Diclofenac acid | Analgesic antiinflammatory |
| Phenytoin | Antiepileptic |

As seen from FIG. 4, the solubility of each drug was found to increase in accordance with the increase in the concentration of the low molecular weight chitosan. A marked increase in the solubility was observed, in particular, for acidic drugs. This may be due to the participation of some interaction, such as the formation of counter ions between the low molecular weight chitosan which is a basic polysaccharide, and the acidic drug. However, an increase in the solubility of the drug was recognized also for steroids, namely, digoxin and phenytoin, for which a consideration for dissociation of the drug may be unnecessary. A dissolution characteristic curve of Bs-type including a rising portion of increasing solubility, a plateau and a falling portion was observed for betamethasone and triamcinolone. These results suggest that the solubility of drug is increased not only by the formation of counter ions between the low molecular weight chitosan and the drug but also by some other interactions possibly occurring between them.

EXAMPLE 4

Drug dissolution rate was examined for each of the solid dispersions and for the drug itself for triamcinolone, metamethasone, prednisolone, flurbiprofen, indomethacin, digoxin and phenytoin.

The rate of dissolution was determined for drug compositions having the low molecular weight chitosan C-5 obtained in Reference Example 1, by observing the concentration of the drug in the same manner as in Example 1 at a regular time interval except that the drug was charged in an amount within the range of from 10 to 30 mg in 60 ml of solution and the agitation was effected at 57 rpm. The ratio of the dissolved amount of drug to the total charged amount of the drug was calculated. Results are summarized in FIGS. 5(A)– 5(G) in a corresponding graph. The experimental results for flurbiprofen are given here again.

The average dissolution time calculated from the rate of dissolution for each drug is recited in Table 3. The calculation of the average dissolution time was made basing on the method given in "Chem. Pharm. Bull.", 30, 1088 (1982).

TABLE 3

| | Average Dissolution Time (min.) | |
| --- | --- | --- |
| Drug | Drug alone | Solid Dispersion |
| Triamcinolone | 24.3 | 2.7 |
| Betamethasone | 45.9 | 1.0 |
| Prednisolone | 18.7 | 1.6 |
| Flurbiprofen | 46.1 | 5.2 |
| Indomethacin | 24.8 | 16.2 |
| Digoxin | 40.9 | 3.8 |
| Phenytoin | 35.9 | 6.4 |

For all the drugs examined, the dissolution rate of the drug from the solid dispersion thereof was found to be a markedly accelerated as compared with that for the drug without any additive. While there may be possible increase in the dissolution rate due to the increase in the solubility of the drug for acidic drugs, as seen from the results of Example 3, it is to be pointed out that a marked increase in the dissolution rate for drugs for which the increase in solubility was not much recognized was observed.

EXAMPLE 5

A physical mixture obtained by simply mixing flurbiprofen with the low molecular weight powder product C-5 as obtained in Reference Example 1 in a weight ratio of 1:3 and a solid dispersion of flurbiprofen with the product C-5 prepared in the same manner as in Example 1, except that the weight mixing proportion was settled to be 1:3, were examined by powder X-ray diffraction. The powder X-ray diffraction examination was carried out by employing an X-ray diffraction apparatus Geiger Flex 2102 of the firm Rigakudenki K.K. with a Ni filter using Cu-Ka ray under the condition of 30 kV, 20 mA, a time constant of 2 sec. and a scanning velocity of 1° C./min.

Similar powder X-ray diffraction examination was carried out also for indomethacin, digoxin and triamcinolone in the same manner as above. The results are recited in FIGS. 6(A)–6(D) in an X-ray diffraction chart.

The powder X-ray diffraction pattern provides informations of the drug about its crystalline structure and its state of cohesion. As seen from FIGS. 6(A)–6(D), characteristic peaks specific for each drug were observed for the physical mixture, since the low molecular weight chitosan is an amorphous substance. For the solid dispersion of acidic drug, namely, flurbiprofen, the characteristic peaks specific for the drug observed for the physical mixture were not detected, indicating that flurbiprofen is present therein in a state finely dispersed within the amorphous mass of the low molecular weight chitosan in a finely disintegrated amorphous form. The three other drugs had X-ray diffraction patterns completely identical with that of the physical mixture also in the solid dispersion and no decrease in the crystallinity of the drug by the admixing of the low molecular weight chitosan.

EXAMPLE 6

Flurbiprofen and indomethacin, which each have a melting point lower than that of the low molecular weight chitosan, were examined by differential thermal analysis. The examinations were made for the physical mixtures and solid dispersions as obtained in Example 5 and the low molecular weight chitosan alone as well as each drug without any additive. The differential thermal analysis was carried out on a differential thermal analyzer Thermoflex TG-8110 of Rigakudenki K.K. using each such an amount of the sample that corresponds to 5 mg of the drug as calculated and employing α-alumina as the reference substance at a heat elevation rate of 10° C./min. The results are recited in FIGS. 7(A) and 7(B).

Figure 7A:
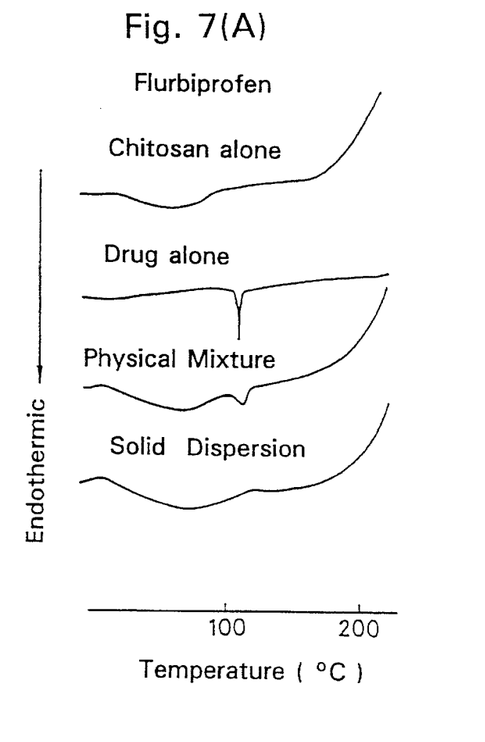
FIGS. 7(A) and 7(B) are graphs showing the results of Example 6.
Figure 7B:
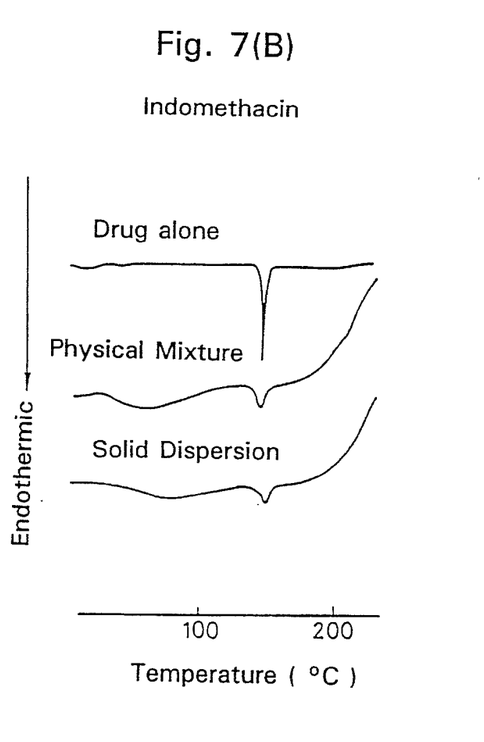

By differential thermal analysis, the physical state of the drug in the solid can be conjectured by observing endothermic peaks over the temperature axis on the chart occurring by possible melting of the drug, as seen from the charts of FIG. 7, which show that the endothermic peak due to melting of the drug has disappeared for the solid dispersion of flurbiprofen, indicating that flurbiprofen is present therein in a state finely dispersed within the mass of said solid dispersion losing its crystalline structure. In the case of indomethacin, the endothermic peak was found also for the solid dispersion, indicating that indomethacin is present therein under dispersion within the mass under preservation of its crystalline structure. These results corresponds to those of Example 5 and it is to be assumed that flurbiprofen is held dispersed within the solid dispersion thereof together with the low molecular weight chitosan in an amorphous state under some interaction with the low molecular weight chitosan in the solid state, while the other drugs cause almost no interaction with the low molecular weight chitosan and will be dispersed within the solid dispersion holding their crystalline structure.

EXAMPLE 7

Flurbiprofen, indomethacin and triamcinolone were examined for evaluating their wetting characteristics with water. Examination was effected for the samples of the solid dispersions as obtained in Example 5 and for each drug alone without any additive. The wetting was evaluated by determining the wetting contact angle of water drops on the surface of a tablet having a diameter of 2 cm obtained using an IR tabletting machine with a drop of water of 50 μl. The results are summarized in Table 4.

TABLE 4

|  | Wetting Contact Angle (°) | |
| --- | --- | --- |
| Drug | Drug alone | Solid Disp. |
| Flurbiprofen | 55 | 30 |
| Indomethacin | 50 | 32 |
| Triamcinolone | 50 | 40 |

As seen from Table 4, the wetting contact angle for the solid dispersion with the low molecular weight chitosan was found to be decrease as compared with that for the drug alone. The results suggest that the low molecular weight chitosan contributes to an increase in the dissolution rate of the poorly water-soluble drugs by improving the wettability by water on the surface of the drug particle.

EXAMPLE 8

Figure 8:
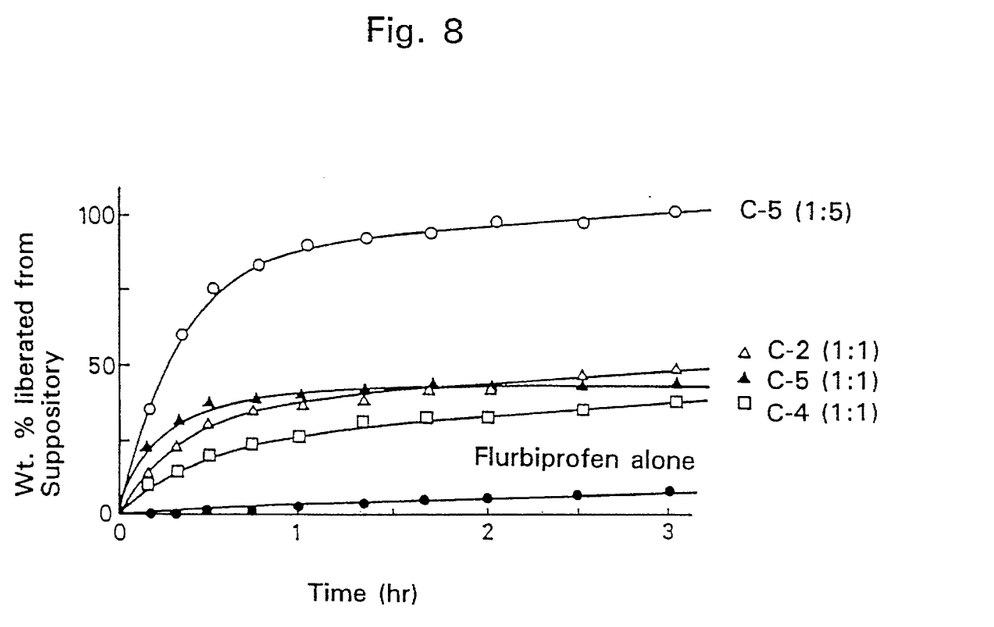
FIG. 8 is a graph showing the results of Example 8.

Suppositories were prepared using H-15 (cacao butter) as the base substance from each of the kneaded mixtures of flurbiprofen with either of the low molecular weight chitosan products C-2, C-4 and C-5 as obtained in Reference Example 1 in a weight ratio of 1:1 or 1:5. Using these suppositories, the liberation rate of flurbiprofen from the suppository was detected. The results are given in FIG. 8 as a graph.

POSSIBILITIES OF APPLICATION IN INDUSTRY

The drug compositions according to the present invention can be utilized for improving the solubility and dissolution rate of various poorly water-soluble drugs for medical and other uses and can be employed as drug compositions for preparing medicinal drugs and other drugs in which the bioabsorptivity and the biouptake of such poorly water-soluble drugs in living organisms is improved.

We claim:

1. A medicinal pharmaceutical composition comprising a medicinal pharmaceutical component having a low water solubility and a water-soluble chitosan derivative having a weight average molecular weight in the range of from 500 to $50 \times 10^3$ and which is soluble in neutral and alkaline water, said water-soluble chitosan derivative being obtained by subjecting high molecular weight chitosan to a molecular weight degradation reaction with an enzyme, hydrogen peroxide, a nitrite ion or an alkali.

2. The medicinal pharmaceutical composition of claim 1, wherein said pharmaceutical component and said water-soluble chitosan derivative are contained in the composition in a proportion of one part of pharmaceutical component per 0.2 to 10 parts of water-soluble chitosan derivative.

3. The medicinal pharmaceutical composition of claim 1, wherein said medicinal pharmaceutical component is selected from the group consisting of betamethasone, diclofenac acid, dicumarol, digoxin, flurbiprofen, ibuprofen, indomethacin, ketoprofen, mefenamic acid, phenytoin, prednisolone, triamcinolone, vitamin E and vitamin K.

4. The medicinal pharmaceutical composition of claim 2, wherein said medicinal pharmaceutical component is selected from the group consisting of betamethasone, diclofenac acid, dicumarol, digoxin, flurbiprofen, ibuprofen, indomethacin, ketoprofen, mefenamic acid, phenytoin, prednisolone, triamcinolone, vitamin E and vitamin K.

5. The medicinal pharmaceutical composition of claim 1, wherein the water-soluble chitosan derivative has a weight average molecular weight of from 800 to $10 \times 10^3$.

6. A method for improving the solubility and rate of dissolution in water of a medicinal pharmaceutical component having a low water solubility comprising the step of mixing the medicinal pharmaceutical component with a water-soluble chitosan derivative having a weight average molecular weight in the range of from 500 to $50 \times 10^3$ and which is soluble in neutral and alkaline water, said water-soluble chitosan derivative being obtained by subjecting high molecular weight chitosan to a molecular weight degradation reaction with an enzyme, hydrogen peroxide, a nitrite ion or an alkali.

7. The method of claim 6, wherein said pharmaceutical component and said water-soluble chitosan derivative are mixed in a proportion of one part of pharmaceutical component per 0.2 to 10 parts of water-soluble chitosan.

8. The method of claim 6, wherein said medicinal pharmaceutical component is selected from the group consisting of betamethasone, diclofenac acid, dicumarol, digoxin, flurbiprofen, ibuprofen, indomethacin, ketoprofen, mefenamic acid, phenytoin, prednisolone, triamcinolone, vitamin E and vitamin K.

9. The method of claim 7, wherein said medicinal pharmaceutical component is selected from the group consisting of betamethasone, diclofenac acid, dicumarol, digoxin, flurbiprofen, ibuprofen, indomethacin, ketoprofen, mefenamic acid, phenytoin, prednisolone, triamcinolone, vitamin E and vitamin K.

10. The method of claim 6, wherein the water-soluble chitosan derivative product has a weight average molecular weight of from 800 to $10 \times 10^3$.

\* \* \* \* \*

UNITED STATES PATENT AND TRADEMARK OFFICE
CERTIFICATE OF CORRECTION

PATENT NO. : 5 474 989
DATED : December 12, 1995
INVENTOR(S) : Masanori HASHIMOTO et al It is certified that error appears in the above-indentified patent and that said Letters Patent is hereby corrected as shown below:

Column 12, line 5; delete "product".

Signed and Sealed this

Twenty-third Day of July, 1996

Attest:

BRUCE LEHMAN

Attesting Officer

Commissioner of Patents and Trademarks